(12) United States Patent
Amin et al.

(10) Patent No.: US 10,933,076 B2
(45) Date of Patent: Mar. 2, 2021

(54) CROCIN-SORAFENIB COMBINATION THERAPY FOR LIVER CANCER

(71) Applicant: United Arab Emirates University, Al Ain (AE)

(72) Inventors: Amr Amin, Al Ain (AE); Basma Awad, Al Ain (AE)

(73) Assignee: UNITED ARAB EMIRATES UNIVERSITY, Al Ain (AE)

( * ) Notice: Subject to any disclaimer, the term of this patent is extended or adjusted under 35 U.S.C. 154(b) by 0 days.

(21) Appl. No.: 16/513,026

(22) Filed: Jul. 16, 2019

(65) Prior Publication Data
US 2021/0015835 A1    Jan. 21, 2021

(51) Int. Cl.
*A61K 31/7024* (2006.01)
*A61P 35/00* (2006.01)
*A61K 31/44* (2006.01)

(52) U.S. Cl.
CPC .......... *A61K 31/7024* (2013.01); *A61K 31/44* (2013.01); *A61P 35/00* (2018.01)

(58) Field of Classification Search
None
See application file for complete search history.

(56) References Cited

U.S. PATENT DOCUMENTS

2014/0141082 A1* 5/2014 Gao ................. A61K 31/05
                                                    424/474

OTHER PUBLICATIONS

Sawant, Biochemical Pharmacology 163 (2019), 32-45, available online Jan. 30, 2019. (Year: 2019).*
Amin, Recent Patents on Anti-Cancer Drug Discovery, 2016, 11, 121-133. (Year: 2016).*
Reiss, Journal of Clinical Oncology, vol. 35, No. 31, Nov. 1, 2017, pp. 3575-3581. (Year: 2017).*
Stenger, Does Reducing the Starting Dose of Sorafenib Affect Outcomes in Hepatocellular Carcinoma?, The ASCO Post, Sep. 19, 2017 (Year: 2017).*

* cited by examiner

*Primary Examiner* — Layla D Berry
(74) *Attorney, Agent, or Firm* — Hayes Soloway P.C.

(57) ABSTRACT

A therapeutic combination of drugs for the treatment of a liver cancer includes a crocin, or a pharmaceutically acceptable pro-drug thereof, and sorafenib. A method of treating, suppressing, or reducing the severity of a liver cancer in a subject, involves administering to the subject a first amount of sorafenib, and administering to the subject a second amount of a crocin or a pharmaceutically acceptable pro-drug thereof.

18 Claims, 12 Drawing Sheets

| Species | Reference body weight (kg) | Working weight range (kg) | Body surface area (m²) | To convert dose in mg/kg to dose in mg/m², multiply by $K_m$ | To convert animal dose in mg/kg to HED in mg/kg, either | |
|---|---|---|---|---|---|---|
| | | | | | Divide animal dose by | Multiply animal dose by |
| Human | 60 | - | 1.62 | 37 | - | - |
| Mouse | 0.02 | 0.011-0.034 | 0.007 | 3 | 12.3 | 0.081 |
| Hamster | 0.08 | 0.047-0.157 | 0.016 | 5 | 7.4 | 0.135 |
| Rat | 0.15 | 0.08-0.27 | 0.025 | 6 | 6.2 | 0.162 |
| Ferret | 0.30 | 0.16-0.54 | 0.043 | 7 | 5.3 | 0.189 |
| Guinea pig | 0.40 | 0.208-0.700 | 0.05 | 8 | 4.6 | 0.216 |
| Rabbit | 1.8 | 0.90-3.0 | 0.15 | 12 | 3.1 | 0.324 |
| Dog | 10 | 5-17 | 0.50 | 20 | 1.8 | 0.541 |
| Monkeys (rhesus) | 3 | 1.4-4.9 | 0.25 | 12 | 3.1 | 0.324 |
| Marmoset | 0.35 | 0.14-0.72 | 0.06 | 6 | 6.2 | 0.162 |
| Squirrel monkey | 0.60 | 0.29-0.97 | 0.09 | 7 | 5.3 | 0.189 |
| Baboon | 12 | 7-23 | 0.60 | 20 | 1.8 | 0.541 |
| Micro pig | 20 | 10-33 | 0.74 | 27 | 1.4 | 0.730 |
| Mini pig | 40 | 25-64 | 1.14 | 35 | 1.1 | 0.946 |

FIG. 12

CROCIN-SORAFENIB COMBINATION THERAPY FOR LIVER CANCER

TECHNICAL FIELD

The present invention relates to therapeutic formulations and methods for treating cancer crocin either alone or in combination with sorafenib.

BACKGROUND

Liver cancer differs according to the type of cells that are involved. They include hepatocellular carcinoma (HCC), cholangiocarcinoma and angiosarcoma. The progression of liver cancer starts with frequent insult to the liver due to several factors. Repeated insults to the liver will cause acute inflammation, when it persists it will lead to fibrosis and cirrhosis and eventually the formation of hepatic neoplasms. HCC is the most prevalent type of primary liver cancer with 782000 cases diagnosed and 746000 deaths in 2012 in the United States alone. HCC is ranked as the fifth most common type of cancer and the third cause of cancer related deaths worldwide. The incidence of liver cancer at UAE is rising due to the increased number of patients suffering from liver diseases that when left untreated would progress into liver cancer. Liver cancer is the fourth cause of cancer related deaths for both genders in the UAE (FIG. 2; Department of Health—Abu-Dhabi, 2015). The escalating incidence of liver cancer is attributed to multiple risk factors including alcoholic consumption, fatty liver disease, viral hepatitis C and B. As it is the case of most cancers, chemotherapy is the first line of defense. Chemotherapeutic drugs used to treat HCC include cisplatin, doxorubicin and mitomycin. All those drugs aim to increase the survival and rarely do they reverse the course of cancer development. One of the major challenges with chemotherapies is their non-selective cytotoxicity. Patients with the best prognosis are the ones who detect their cancer at early stages and opt for surgical resection of the tumor and undergoing liver transplantation. In most cases, however, patients are diagnosed with liver cancer at late stages where intervention opportunities are limited and not very effective in most cases.

Sorafenib is the only U.S. Food and Drug Administration (FDA) approved targeted therapy for HCC. Sorafenib, an oral multikinase inhibitor, blocks tumor cell proliferation by targeting Raf/MEK/ERK signaling and inhibits angiogenesis by targeting vascular endothelial growth factor (VEGF) and platelet-derived growth factor (PDGF) receptors. Despite the benefit provided by sorafenib, the need for additional advanced HCC treatment options is much needed. Compared with monotherapy, combination therapy targeting multiple signaling pathways may be a better treatment option by providing a way to potentially circumvent resistance, feedback activation, and compensatory activation of pro-survival pathways.

Crocetin di-gentiobiose ester known as crocin has been found to be the primary compound in saffron. Crocin is one of the few carotenoids that are water soluble. Crocin demonstrates many pharmacological properties and have been confirmed as a powerful antioxidant and anti-inflammatory effects. Treatments with crocin and cisplatin individually or jointly on osteosarcoma cells MG63 and OS732 cells showed a strong killing effect on osteosarcoma cells and suppressed the ability of invasion of MG63 cells which leads to the upregulation of the expression of caspase-3 and caspase-8 all of which are markers that indicate the activation of apoptosis. In a research conducted to test the effect of crocin coated nanoparticles on precancerous livers in mice showed a significant regression of the precancerous lesions and upregulation of apoptosis. Another research showed crocin's ability to prevent early lesions of liver cancer in HepG2 cells and Wistar rats. Crocin has been shown to inhibit proliferation of colorectal cancer (HCT116 wild type and HCT116 p53-/-cell lines), crocin treatment induced an autophagy-independent classical programmed cell death.

SUMMARY OF THE EMBODIMENTS

In accordance with a first aspect of the present disclosure, there is provided a method of treating, suppressing, or reducing the severity of a liver cancer in a subject, the method comprising: administering to the subject a first amount of sorafenib, and administering to the subject a second amount of a crocin or a pharmaceutically acceptable pro-drug thereof. In an embodiment, the crocin is α-crocin. The crocin or its pro-drug and the sorafenib may be compounded together in a composition including both compounds. Alternatively, the crocin or its pro-drug and the Sorafenib may be administered separately in separate pharmaceutical compositions. The crocin or its pro-drug and the sorafenib may be administered together or in a sequential manner. For example, the crocin or its pro-drug may be administered first to sensitize the cancer cells prior to exposure to the sorafenib, and the sorafenib may be administered second. Example crocin pro-drugs include crocin salts, hydrates, hemiacetals, acetals, thioacetals, silylethers, tautomers, isomers, and combinations thereof. The liver cancer may be hepatocellular carcinoma (HCC), fibrolamellar HCC, cholangiocarcinoma, angiosarcoma, and/or metastatic liver cancer.

In accordance with a second aspect of the invention, there is provided a therapeutic combination of drugs for the treatment of a liver cancer, the combination comprising: a crocin or a pharmaceutically acceptable pro-drug thereof, and sorafenib. In non-limiting embodiments, the crocin is selected from the group consisting of monoglycosyl polyene esters of crocetin, diglycosyl polyene esters of crocetin, and combinations thereof. In an example embodiment, the crocin is α-crocin. The pro-drug may be selected from the group consisting of a crocin salt, hydrate, hemiacetal, acetal, thioacetal, silylether, tautomer, isomer, and combinations thereof. The crocin and the sorafenib may be compounded together in a same unitary pharmaceutical composition including both compounds. Alternatively the crocin and the sorafenib may be provided in separate pharmaceutical compositions. The amount of the sorafenib is 0.1:1 to 10:1 by weight, with respect to the content of the crocin of the combination. Also provided is a method of treating, suppressing, or reducing the severity of a liver cancer in a subject, the method comprising administering to a subject a therapeutically effective amount of the therapeutic combination of drugs of this second aspect of the invention.

In accordance with a third aspect of the invention, there is provided an improved therapeutic method of treating, suppressing, or reducing the severity of a liver cancer in a subject. The method comprises: administering a first amount of sorafenib, and the improvement comprises: administering to the subject a second amount of a crocin. In an example embodiment, the crocin is α-crocin. The crocin and the sorafenib may be compounded together in a same unitary pharmaceutical composition including both compounds or separately, for example in separate containers provided in a kit.

BRIEF DESCRIPTION OF THE FIGURES

The invention can be better understood with reference to the following figures and description. The components in the figures are not necessarily to scale and are not intended to accurately represent molecules, cells, cell organelles, tissues, or their interactions, emphasis instead being placed upon illustrating the principles of the invention.

FIG. 12 is a table reporting human equivalent dose (HED) dosage factors based on body surface area of other species according to data obtained from Food and Drug Administration draft guidelines.

DETAILED DESCRIPTION OF SPECIFIC EMBODIMENTS

Figure 1:
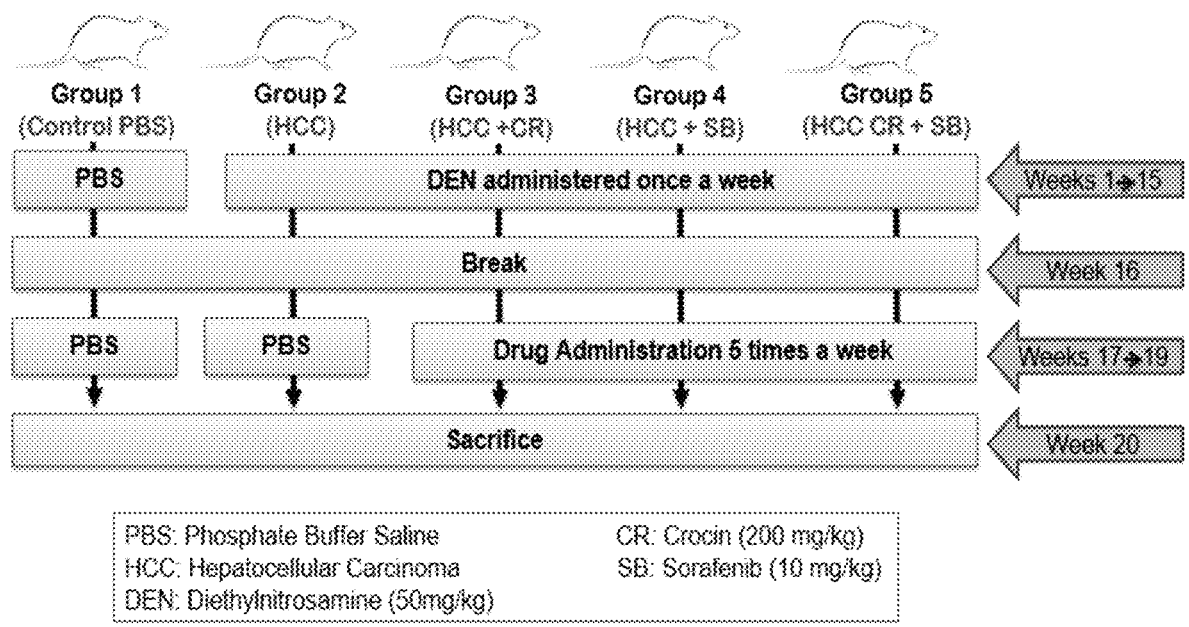
FIG. 1 illustrates the experimental design that was followed in the study reported in the present application.

A study was undertaken to examine crocin's therapeutic effects against chemically induced hepatocellular carcinoma. First, HCC was chemically induced in male Wistar rats. Treatment with crocin followed, and biomarkers of liver function were assessed. Liver tissues were then subjected to histopathological evaluation, and key tumor markers were examined by western blotting. Based on the biochemical, histological, and molecular markers evaluated in this study, saffron-based crocin proves to be a potent novel therapeutic candidate against DEN-induced HCC.

The study also uncovered surprising superior therapeutic effects of crocin administered in combination therapy with sorafenib. Hence, the present invention is at least in part based on the finding that crocin and sorafenib exert a synergistic anticancer effect on HCC in laboratory rats. This therapeutic effect can be put to use in the treatment of liver cancer. Compared with monotherapy with sorafenib alone, treatment with crocin in combination with sorafenib targeting multiple signaling pathways offers a better treatment alternative. Without being bound to any particular theory, it is believed that treatment with crocin triggers the activation of the intrinsic apoptotic pathway in liver cancer cells. Intriguingly, combination treatment of crocin and sorafenib seemed to have a better effect in the activation of the intrinsic apoptotic pathway over the treatment with crocin alone or sorafenib alone. This finding can be described as a synergy, or greater than additive effect, that is specific to certain combinations of sorafenib and crocin, and liver cancer, with a higher improvement than with monotherapy with either crocin or sorafenib.

In exemplary embodiments, provided herein are therapeutic combinations of drugs including a first amount of crocin (or its pharmaceutically acceptable pro-drug) and a second amount of sorafenib. Essentially, the combination of crocin and sorafenib represents a therapeutic combination that may be more efficacious than either agent alone or the simple sum of the two agents. In addition, different doses of the combination may lead to additional gains in treatment of the liver cancer than either crocin or sorafenib alone. Accordingly, in some embodiments, the present application provides unexpectedly advantageous methods and compositions for treating liver cancer, whereby sorafenib and a crocin are administered in a ratio that is particularly effective (e.g., synergistic or more than additive).

CROCIN

Chemically, crocin is the diester formed from the disaccharide gentiobiose and the dicarboxylic acid crocetin:

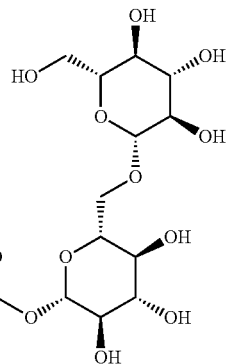
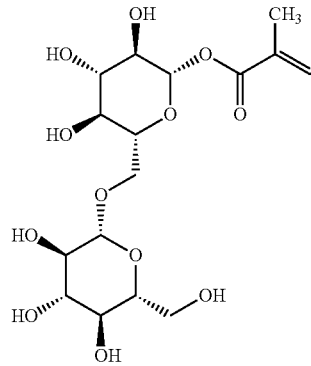

Crocin

When isolated as a pure chemical compound, crocin has a deep red color and forms crystals with a melting point of 186° C. When dissolved in water, it forms an orange solution. The term crocins in a broad sense may also refer to members of a series of related hydrophilic carotenoids that are either monoglycosyl or diglycosyl polyene esters of crocetin. The crocin underlying saffron's aroma is α-crocin (trans-crocetin di-(β-D-gentiobiosyl) ester) and bears the systematic (IUPAC) name 8,8-diapo-8,8-carotenoic acid. The major active component of saffron is the yellow pigment crocin 2 (three other derivatives with different glycosylations are known) containing a gentiobiose (disaccharide) group at each end of the molecule.

A composition including crocin may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of crocin include those suitable for parenteral (including subcutaneous, intravenous, intramedullary, intraarticular, intramuscular, or intraperitoneal injection), rectal, topical, transdermal, or oral (for example, in capsules, suspensions, or tablets) administration. The formulations may conveniently be presented in unit dosage form and may be prepared by any methods well known in the art of pharmacy. The amount of crocin or its pharmaceutically acceptable pro-drugs which can be combined with a carrier material to produce a single dosage form will vary depending upon the subject being treated and the particular mode of administration. The amount of an active ingredient which can be combined with a carrier material to produce a single dosage form will usually be that amount of the compound which produces a therapeutic effect. Usually, out of one hundred percent, this amount will range from about 1 wt % to about 99 wt % of active ingredient, preferably from about 5 wt % to about 70 wt %, most preferably from about 10 wt % to about 30 wt %.

Regardless of the route of administration selected, crocin or its pro-drugs may be formulated into pharmaceutically-acceptable dosage forms by conventional methods known to those of skill in the art. Crocin may be formulated for administration in any convenient way for use in human or veterinary medicine, by analogy with other pharmaceuticals.

SORAFENIB

In various embodiments, the present invention includes the use of sorafenib, for example in the form of sorafenib tosylate as well as other pharmaceutically acceptable forms, salts, and esters of sorafenib. Sorafenib is commercially available as NEXAVAR®, which is the tosylate salt of sorafenib. Sorafenib tosylate has IUPAC chemical name 4-(4-{3-[4-Chloro-3 (trifluoromethyl)phenyl]ureido} phenoxy) N-methylpyridine-2-carboxamide 4-methylbenzenesulfonate and its structural formula is:

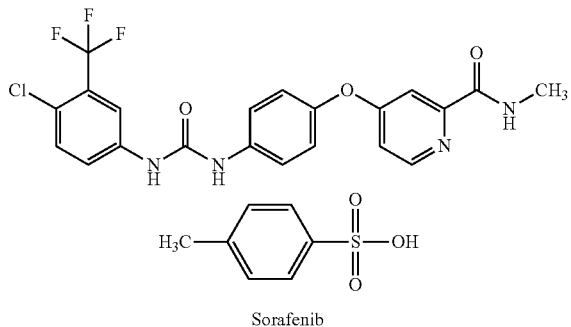

Sorafenib

The recommended daily dose of sorafenib tosylate is 800 mg administered as 400 mg (two tablets) orally twice daily. However, treatment interruption and/or dose reduction may be needed to manage suspected adverse drug reactions. In such instances, the dose may be reduced to 400 mg once daily or to 400 mg every other day. A person of ordinary skill will understand that sorafenib dosage and administration can follow medically approved guidelines, as well medically accepted deviations or alterations to such guidelines.

LIVER CANCER

In one aspect, the present invention provides methods for the treatment of liver cancer cells, including cancer cells in a subject or in vitro treatment of isolated cancer cells. If the cancer cells are in a subject, the subject may be a primate, such as a human, with liver cancer. The subject may be a mammal. The subject may be an adult human (i.e., 18 years or older), or a juvenile human (i.e., less than 18 years old). In various embodiments, the liver cancer may be a hepatocellular carcinoma (HCC), a fibrolamellar HCC, a cholangiocarcinoma, an angiosarcoma, or a metastatic liver cancer.

In some embodiments, the liver cancer is not resistant to sorafenib. Alternatively, the liver cancer may have primary or secondary resistance to sorafenib. The subject can be a responder to sorafenib in the absence of the crocin. The subject can be a non-responder to sorafenib in the absence of crocin. In some embodiments, the subject has undergone a prior treatment with sorafenib lasting at least 1, 2, 4, 6, 8, 10 months or longer. In other embodiments, the subjects are patients who have experienced one or more significant adverse side effect to sorafenib and therefore require a reduction in dose.

In some embodiments, the liver cancer is intermediate, advanced, or terminal stage. The liver cancer can be metastatic or non-metastatic. The liver cancer may be resectable or unresectable. The liver cancer may include a single tumor, multiple tumors, or a poorly defined tumor with an infiltrative growth pattern (into portal veins or hepatic veins). The liver cancer may include a fibrolamellar, pseudoglandular (adenoid), pleomorphic (giant cell), or clear cell pattern. The liver cancer may include a well differentiated form, and tumor cells resemble hepatocytes, form trabeculae, cords, and nests, and/or contain bile pigment in cytoplasm. The liver cancer may include a poorly differentiated form, and malignant epithelial cells are discohesive, pleomorphic, anaplastic, and/or giant. In some embodiments, the liver cancer may be associated with hepatitis B, hepatitis C, cirrhosis, or type 2 diabetes.

In some embodiments, the subject is a human having an Eastern Cooperative Oncology Group (ECOG) performance status≤2. In some embodiments, the subject is a human having acceptable liver function defined as (i) total bilirubin≤1.5 times the upper limit of normal (ULN); for patients with hepatocellular carcinoma only, total bilirubin≤3 mg/dL (i.e., Child-Pugh Score for bilirubin is no greater than 2); (ii) aspartate aminotransferase (AST), alanine aminotransferase (ALT) and alkaline phosphatase (ALP)≤5×ULN; or (iii) acceptable renal function: Serum creatinine≤1.5 times the ULN, or calculated creatinine clearance≥60 mL/min/1.73 m² for patients with creatinine levels above 1.5 times the institutional normal.

In some embodiments, the subject is a human having acceptable hematological status defined as (i) absolute Neutrophil Count (ANC)≥1500 cells/mm³; (ii) platelet count≥100,000 plts/mm³ (without transfusion); ≥75,000 plts/mm³ for patients with hepatocellular carcinoma only; or (iii) hemoglobin≥9 g/dL.

In some embodiments, the subject is a human having a prothrombin time (PT) or International Normalized Ratio (INR)≤1.25×ULN; INR<1.7 or prothrombin time (PT) or <4 seconds above ULN (i.e., Child-Pugh Score is no greater than 1 for the coagulation parameter); or serum albumin>2.8 g/dL (i.e., Child-Pugh Score for albumin is no greater than 2).

COMBINATION THERAPY

Combination therapy or polytherapy is the use of more than one medication or other therapy, as opposed to monotherapy, which is any therapy taken alone. In one aspect of the present invention, provided herein is a therapeutic combination of drugs for the treatment of liver cancer, the combination including crocin and sorafenib. In an example embodiment of the combination, the crocin and sorafenib are compounded together in a same unitary pharmaceutical composition including both compounds. In another example embodiment, the crocin and sorafenib are in separate pharmaceutical compositions. Also provided are methods for treating, suppressing, or reducing the severity of a liver cancer in a subject by administering to the subject a therapeutic amount of the combination.

In some embodiments, the therapeutic combination refers to using specific combinations (e.g., ratios and/or dosing schedules) of crocin and sorafenib. More particularly, the invention provides therapeutic combinations and methods for treating liver cancer where the crocin and sorafenib are administered in a ratio that is particularly effective (e.g., synergistic or more than additive). In representative embodiments, the ratio, that is, the mass-to-mass ratio of crocin:sorafenib is about 50 to 1, 40 to 1, 30 to 1, 25 to 1, 20 to 1, 10 to 1, 5 to 1, 2 to 1, 1 to 2, 1 to 5, 1 to 10, 1 to 20, 1 to 30, 1 to 40, or 1 to 50. In some embodiments, the ratio is, or is at least, about 1, 2, 5, 10, 12, 15, 20, or 50. In some embodiments, the ratio is less than about 5, 10, 15, 20, 30, 40, 50, 60, or 70. Example weight-to-weight ratios are about 1, 2, 5, 8, 10, 15, 20, 25, 30, 40, and 50.

The mass-to-mass ratio of crocin:sorafenib can be measured over different periods of time. For example, the mass ratio may be based on the respective amounts of crocin and sorafenib administered to the subject in a single day, a single week, 14 days, 21 days, or 28 days.

The sorafenib dosing amount and/or schedule can follow clinically approved, or experimental, guidelines. In various embodiments, the dose of sorafenib is about 800, 600, 400, or 200 mg/day. A 200 mg/day dose can be administered as a 400 mg dose every other day.

Likewise the crocin dosing amount and/or schedule can follow clinically approved, or experimental, guidelines. Also, the data obtained from animal studies may be used in formulating a crocin range of dosage for use in humans. For example, effective dosages achieved in one animal species may be extrapolated for use in another animal, including humans, as illustrated in the conversion table of FIG. 12 where human equivalent dose (HED) dosage factors based on body surface area of other species are reported. In exemplary embodiments, the dose of crocin fall in the range from about 0.001, 0.01, 0.1, 0.5, 1, 10, 15, 20, 25, 50, 100, 200, 300, 400, 500, 600, or 750 to about 1000 mg/day per kg body weight of the subject. In certain embodiments, the dose of crocin will typically be in the range of about 100 mg/day to about 1000 mg/day per kg body weight of the subject, specifically in the range of about 200 mg/day to about 750 mg/day per kg, and more specifically in the range of about 250 mg/day to about 500 mg/day per kg. In an embodiment, the dose is in the range of about 50 mg to about 250 mg per kg/day. In a further embodiment, the dose in the range of about 100 mg to about 200 mg per kg. In an embodiment, the dose is in the range of about 15 mg/day to 60 mg/day per kg. In a further embodiment, the dose is in the range of about 20 mg/day to 50 mg/day per kg. In an additional embodiment, the dose is in the range of about 25 mg/day to 45 mg/day per kg.

The dose of crocin can be set, within a therapeutically effective range, based upon a selected ratio and dose of sorafenib. As discussed above, the ratio can be determined using the amount of sorafenib administered to a subject over a single day, a single week, 14 days, 21 days, or 28 days.

In some embodiments, the crocin is administered to the subject in 1, 2, 3, 4, 5, 6, or 7 daily doses over a single week (7 days). The crocin may be administered to the subject in 1, 2, 3, 4, 5, 6, 7, 8, 9, 10, 11, 12, 13, or 14 daily doses over 14 days. The crocin may be administered to the subject in 1, 2, 3, 4, 5, 6, 7, 8, 9, 10, 11, 12, 13, 14, 15, 16, 17, 18, 19, 20, or 21 daily doses over 21 days. The crocin may be administered to the subject in 1, 2, 3, 4, 5, 6, 7, 8, 9, 10, 11, 12, 13, 14, 15, 16, 17, 18, 19, 20, 21, 22, 23, 24, 25, 26, 27, or 28 daily doses over 28 days.

In various embodiments, the crocin is administered for: 2 weeks (total 14 days); 1 week with 1 week off (total 14 days); 3 consecutive weeks (total 21 days); 2 weeks with 1 week off (total 21 days); 1 week with 2 weeks off (total 21 days); 4 consecutive weeks (total 28 days); 3 consecutive weeks with 1 week off (total 28 days); 2 weeks with 2 weeks off (total 28 days); 1 week with 3 consecutive weeks off (total 28 days).

In further embodiments, the crocin is: administered on day 1 of a 7, 14, 21 or 28 day cycle; administered on days 1 and 15 of a 21 or 28 day cycle; administered on days 1, 8, and 15 of a 21 or 28 day cycle; or administered on days 1, 2, 8, and 15 of a 21 or 28 day cycle. The crocin can be administered once every 1, 2, 3, 4, 5, 6, 7, or 8 weeks.

A course of crocin-sorafenib therapy can be continued until a clinical endpoint is met. In some embodiments, the therapy is continued until disease progression or unacceptable toxicity occurs. In some embodiments, the therapy is continued until achieving a pathological complete response rate defined as the absence of liver cancer (e.g., HCC). In some embodiments, the therapy is continued until partial or complete remission of the liver cancer. Administering the crocin and the sorafenib to a plurality of subject having liver cancer may increase the Overall Survival (OS), the Progression free Survival (PFS), the Disease Free Survival (DFS), the Response Rate (RR), the Quality of Life (QoL), or a combination thereof.

In various embodiments, the treatment reduces the size and/or number of the liver cancer tumor(s). The treatment can prevent the liver cancer tumor(s) from increasing in size and/or number. The treatment can prevent the liver cancer tumor(s) from metastasizing.

In the methods of the invention, administration of the crocin and sorafenib is not limited to any particular delivery system and may include, without limitation, one or more of parenteral (including subcutaneous, intravenous, intramedullary, intraarticular, intramuscular, or intraperitoneal injection), rectal, topical, transdermal, or oral (for example, in capsules, suspensions, or tablets). Administration to an individual may occur in a single dose or in repeat administrations, and in any of a variety of physiologically acceptable pro-drug or salt forms, and/or with an acceptable pharmaceutical carrier and/or additive as part of a pharmaceutical composition. Physiologically acceptable salt forms and standard pharmaceutical formulation techniques, dosages, and excipients are well known to persons skilled in the art. Additionally, effective dosages achieved in one animal may be extrapolated for use in another animal, including humans, using conversion factors known in the art.

The combination therapies of the invention are not specifically limited to any particular course or regimen and may be employed separately or in conjunction with other therapeutic modalities (e.g., chemotherapy or radiotherapy).

In some embodiments, the crocin is administered prior to the sorafenib, concurrently with the sorafenib, after the sorafenib, or a combination thereof. The crocin may be administered systemically or regionally.

A combination therapy in accordance with the present invention can include additional therapies (e.g., pharmaceutical, radiation, and the like) beyond the crocin and sorafenib. Similarly, the present invention can be used as an adjuvant therapy (e.g., when combined with surgery). In various embodiments, the subject is also treated by surgical resection, percutaneous ethanol or acetic acid injection, transcatheter arterial chemoembolization, radiofrequency ablation, laser ablation, cryoablation, focused external beam radiation stereotactic radiotherapy, selective internal radiation therapy, intra-arterial iodine-131-lipiodol administration, and/or high intensity focused ultrasound.

The combination of the crocin and sorafenib can be used as an adjuvant, neoadjuvant, concomitant, concurrent, or palliative therapy. The combination of the crocin and sorafenib can be used as a first line therapy, second line therapy, or crossover therapy.

In some embodiments, the therapeutically effective dose of sorafenib is reduced through combination with crocin. For example, the daily, weekly or monthly dose of sorafenib can be reduced by at least 10%, 20%, 30%, 40%, 50%, 60%, 70%, 80%, 90% or more relative to the maximum recommended dose or the maximum tolerated dose. In other embodiments, sorafenib is administered at an effective dose that is at least 30%, 40%, 50%, 60%, 70%, 80%, 90% or more below the dose needed to be effective in the absence of crocin administration. In some embodiments, the IC50 of sorafenib is reduced by at least 2-, 4-, 5-, 10-, 20-, 30-, 40-, 50-, or 100-fold relative to the IC50 in the absence of crocin.

KITS

The present invention also provides kits for treating liver cancer. For example, a kit may include one or more pharmaceutical compositions of crocin and sorafenib as described above. The compositions may be pharmaceutical compositions comprising a pharmaceutically acceptable excipient. In other embodiments involving kits, there is provided a kit including a first pharmaceutically acceptable composition including crocin, a second pharmaceutically acceptable composition including sorafenib, and optionally instructions for their use in the treatment of liver cancer. In still other embodiments, there is provided a kit including one more pharmaceutical compositions and one or more devices for accomplishing administration of such compositions. For example, a subject kit may comprise a pharmaceutical composition and catheter for accomplishing direct intraarterial injection of the composition into a cancer. In an embodiment, the device is an intraarterial catheter.

EXPERIMENTAL RESULTS

In Vivo Model: Animals

Male Wistar rats were obtained from the animal research facility at the College of Medicine and Health Sciences, UAE University. Initially animals weighed around 110 gm, they were housed at 12 hours' light/dark cycles at 24-26° C. and maintained on standard laboratory animal diet with food and water ad libitum. All animal experimentations were carried out in accordance with and the approval of the Animal Research and Ethics Committee of the College of Medicine and Health Sciences, UAEU (Approval No. A8-15).

Experimental Design

Carcinogenesis

In this study, 4 weeks old male Wistar rats were used. The rats were randomly divided into two groups; Control group (n=8) which received 1× PBS via intraperitoneal (i.p.) injection; Experimental group which were injected with DEN at 50 mg/kg b. wt. (Sigma Aldrich, USA) dissolved in PBS once a week for 16 weeks via i.p. This HCC induction protocol was modified from the protocol described by (De-Peralta et al., 2016; Schiffer et al., 2005).

Treatment Protocol

At week 16, HCC was established in the experimental group, the animals were divided into 4 groups (n=8) as follows: HCC alone, HCC+crocin, HCC+sorafenib, HCC+crocin+sorafenib (FIG. 1). From week 17 to week 19 treatment with crocin and/or sorafenib was started once a day for five days a week. All drugs were orally administered with intragastric (gavage) tube. Doses and route of administration followed what was been previously reported in the literature.

During the first week of the experiment, the PBS group received 1× PBS via i.p. injection for the entire duration of the experiment. The HCC experimental groups were however injected with 50 mg/kg b.wt. DEN (Sigma Aldrich, USA) dissolved in PBS once a week for 16 weeks. At week 17, treatments with crocin and sorafenib were administered 5 times a week by oral gavage until week 19.

In the HCC+crocin group, crocin (Sigma Aldrich, USA) was administered at a dose of 200 mg/kg b.wt. For the HCC+sorafenib group, sorafenib (Carbosynth Limited) was administered at a dose of 10 mg/kg b.wt. Animals of the HCC+crocin+sorafenib group received crocin at 200 mg/kg b.wt., followed immediately with sorafenib at 10 mg/kg b.wt. Crocin was diluted with 1× PBS. A 0.3% solution of DMSO was used to dissolve the sorafenib. Oral LD50 of crocin is 1-5 g/kg b.wt. for male Wistar rats delivered via i.p. injection. At the end of the experimental period and after a 24-hour post last drug administration, animals were euthanized using Diethyl ether and sacrificed and dissected under controlled conditions. Blood and liver tissue samples were collected and stored either at room temperature in buffered formalin for histological analysis or at −80 C in PBS for biochemical and immunoblotting analyses.

Sample Preparation

Blood Samples

To collect blood samples, the rats were euthanized and then decapitated and blood was collected in collection tubes (BD Vacutainer). To separate the serum from the whole blood the samples were centrifuged at 1200 rpm for 10 minutes. Serum was collected and flash frozen in liquid nitrogen and then stored at −80° C. for further investigation.

Biochemical Analysis

Figure 2:
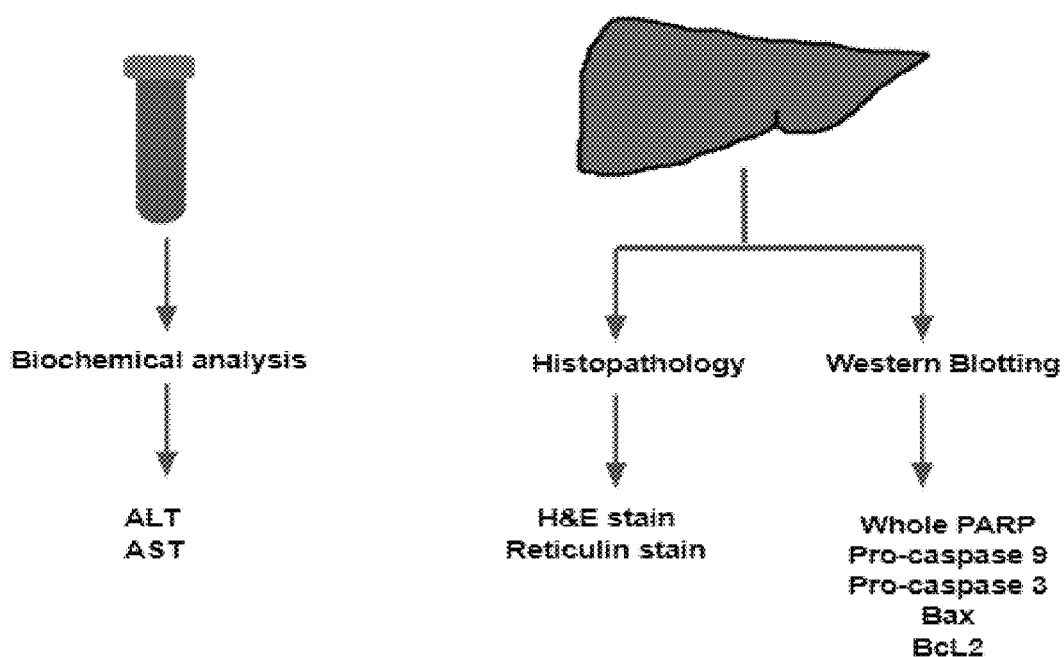
FIG. 2 is a diagrammatic representation of blood and liver samples that were used to assess several parameters.

Levels of liver enzymes Alanine Transaminase (ALT), and Aspartate Aminotransferase (AST) were assessed using a colorimetric assay available commercially. The kits were purchased from Abcam (Cambridge, United Kingdom) and the protocol provided was followed to measure the concentration of ALT and AST using the Promega GloMax Discover microplate reader (FIG. 2).

Liver Samples

The liver tissues were cleaned using PBS and photographs of the liver gross were taken. Each collected liver was then divided into two parts, one part was stored in empty Eppendorf tubes and immediately flash frozen in liquid nitrogen and later stored in −80° C. for further investigation. The other part of the liver was stored in a 10% solution of neutral buffered formalin at room temperature for histopathological examination (FIG. 2).

Hystopathological Preparation

Liver tissue samples were kept in 10% solution of neutral buffered formalin for fixation in order to preserve the integrity of the tissue. Following this step, the tissues were cut into 3 μm thick sections, tissue sections were dehydrated to remove the water content of the tissue, and this process was achieved using a series of ethanol solutions with increasing concentration. Thereafter, xylene was used to clear any ethanol that remained in the tissue to allow the next step to be successful. The final step was to prepare the paraffin blocks by embedding the tissue sections in paraffin wax that allows the wax to infiltrate the tissue. The resulting blocks were then cut into 3 μm thick sections. To observe morphological changes at the cellular levels two stains were used, H&E and reticulin staining. Protocols according to the manufacturer's instructions (Abcam) were followed, and the tissue slides were then observed and examined under light microscopy. All liver tissue samples were blindly examined by a pathologist from Tawam Hospital—UAE to evaluate the effectiveness of the carcinogenesis model and the impact of treatments used in this study.

Western Blot Analysis

Liver tissue samples (10 mg) were homogenized in cold RIPA buffer (Sigma Aldrich, USA) 2 μl of protease inhibitor and of phosphatases inhibitor were added to the homogenizing buffer (Sigma Aldrich, USA). Protein concentration of each liver sample was determined using the Bradford method (Bio-Rad, Hercules, Calif.) with the Promega GloMax Discover. In order to blot the proteins into the gel, 2-mercaptoethanol, a loading dye, was added to the cell lysate produced from the homogenization of liver tissues. The mixture of the lysate and loading dye was then loaded into the SDS-PAGE gel. Variations of gel percentages were used according to the size of protein to be determined. Following the separation of the protein content of each sample on the SDS-PAGE gel, proteins were transferred onto a PVDF membrane and blocked in 5% BSA in TBST or a 5% (w/v) non-fat milk at room temperature for one hour. After the blocking stage, the membranes were incubated with primary anti-body overnight at 4° C. In this study, the primary antibodies selected here were anti-Proliferating Cell Nuclear Antigen (PCNA), anti-caspase-3 (Cell Signaling Technology Inc.), anti-caspase-9 (Nous Biologicals), anti-PolyADP-ribose Polymerase (PARP), anti-Bcl-2, anti-Bax (Santa Cruz). Following the overnight incubation with primary antibodies, the membranes were extensively washed with TBST and re-probed with secondary antibodies including anti-rabbit IgG (Cell Signaling Technology, Inc, MA, USA) and anti-mouse IgG, and conjugated horseradish peroxidase for 1 hour at room temperature. Protein bands were then detected using a chemiluminescence solution known as WesternSure PREMIUM, the signal was detected and visualized using the Bio-Rad ChemiDoc XRS+ System. The intensity of the band was measured using the ImageJ software. The internal control used was total protein which was stained using the SYPRO Ruby protein gel stain following the protocol instructed by the manufacturer (Thermo Fisher Scientific).

Total Protein

Housekeeping proteins are used as the controls for every western blot analysis. Because of their stable expression in tissues, they are great indicators to validate the integrity of the protein samples loaded into the SDS-PAGE gel, therefore accurately reflecting the amount of proteins in the samples. Current research has investigated the ability of these housekeeping proteins to remain stable under different experimental conditions. In this study, various housekeeping proteins were used as loading controls including GAPDH, β-actin, β-tubulin and were found to be inconsistent. In a research paper published in 2003 where this tissue is highlighted, it is indicated that the gene expression of commonly used loading controls including GAPDH and β-actin was increased and varied between 7- to 23-fold and, interestingly, this was shown in cancer tissues (Kim & Kim, 2003). Therefore, an alternative approach was used to resolve this issue. Total protein was utilized as the loading control; this protocol measures the whole protein content of a sample rather than relying on one protein. This has been proven to be a reliable loading control in colorectal cancer and HCC.

RESULTS

Liver Enzymes in Serum

Liver function analyses were carried out to assess the level of enzymes released by hepatocytes into the blood stream. These levels reflect on the integrity and functionality of the liver. When the liver is damaged, these enzymes are extensively released from the hepatocytes. ALT and AST are the most commonly checked enzymes to evaluate the efficiency of the liver.

Effect of Treatment on Serum Enzymes

ALT ($P<0.01$) and AST levels were significantly increased in the HCC group in comparison to the control group, thus indicating the severity of the liver damage due to tumor formation. Treatment with crocin alone and in combination with sorafenib showed a decrease in the level of ALT ($P<0.01$) in comparison to the HCC group. Monotherapy with crocin and combined treatment with both crocin and sorafenib had significantly decreased levels of ALT ($P<0.05$) in comparison to the sorafenib alone group (HCC+sorafenib).

Anti-Cancer Effect of Crocin on DEN-Induced HCC in Rats

Macroscopic Appearance of Liver

Figure 3:
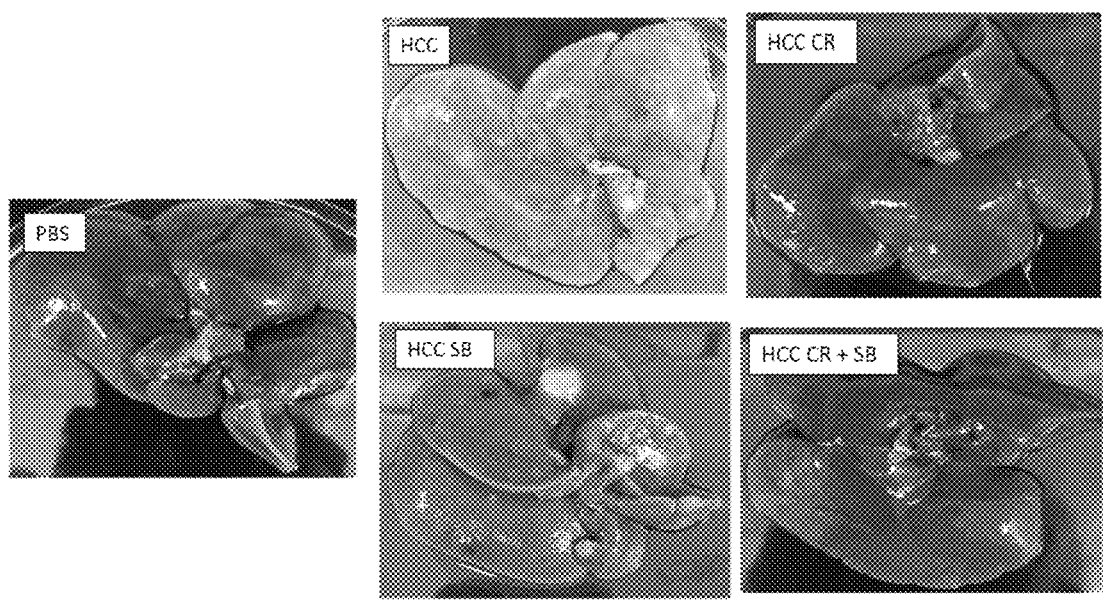
FIG. 3 includes representative images of animal livers to show the therapeutic anti-tumor effect of drugs used. PBS, DEN-induced HCC rats (HCC) or treated with crocin (HCC CR), sorafenib (HCC SB) separately or in combination (HCC CR+SB).
Figure 4:
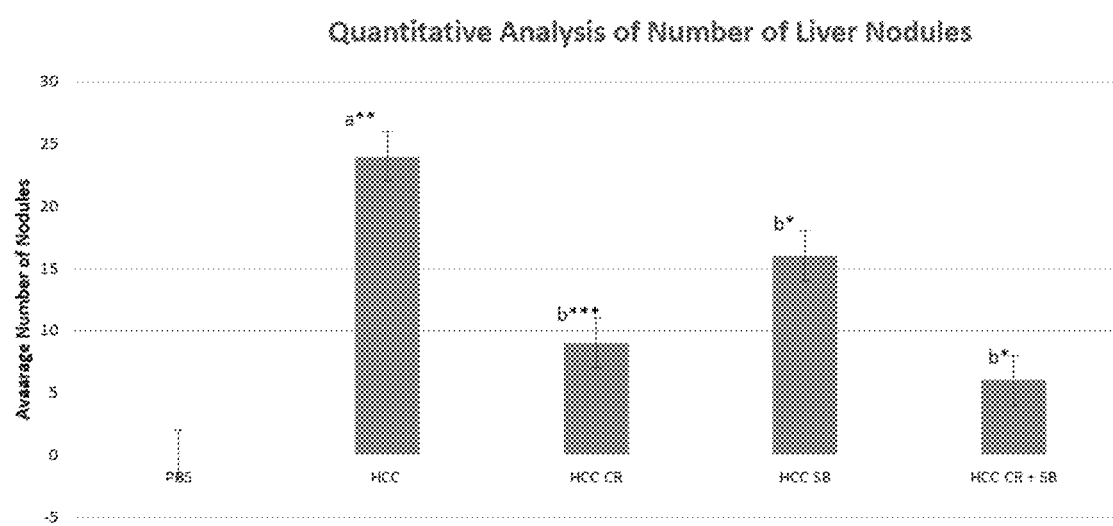
FIG. 4 is a quantitative analysis of number of liver nodules from DEN-induced HCC in rats untreated (HCC alone group), or treated with sorafenib (HCC+sorafenib), crocin (HCC Crocin) separately or in combination (HCC crocin+sorafenib). Statistical significance was determined using Microsoft Excel Data Analysis Too Pack, t-test; two-sample assuming equal variance (a versus PBS, b versus HCC; *P<0.05, **<0.01).

Animal livers in the PBS group had normal structure, size, texture and a glossy dark brown color with no macroscopic lesions observed. HCC livers showed a notable pale color and appearance with multiple lesions that were apparent to the naked eye (FIG. 3). Treated livers appeared less stressed in comparison to the HCC group. Therapeutic administration of drugs to DEN-induced HCC rats restored the normal morphology of the liver compared to those in the HCC alone group. Treatment with crocin alone (HCC+CR) and with both crocin and sorafenib (HCC+CR+SB) reduced the number of lesions in comparison to the HCC animals. Crocin-treated animals exhibited significantly lower numbers of lesions in comparison to the livers of sorafenib alone (HCC+SB) (FIG. 4).

Histopathological Evaluation of Liver

Figure 10:
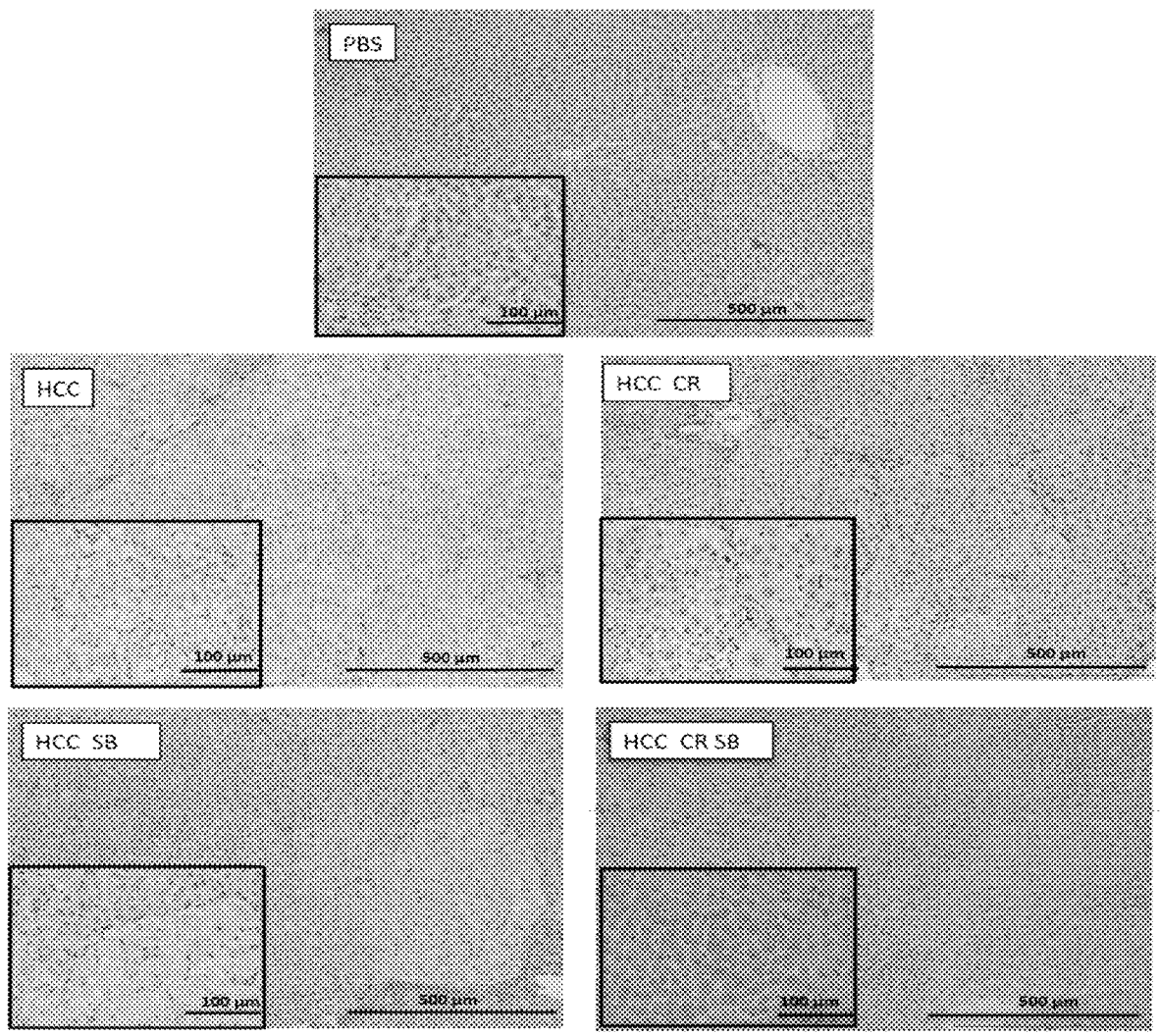
FIG. 10 includes representative images from a histopathological evaluation of livers from control and experimental groups. Control group (PBS), DEN-induced HCC in untreated rats (HCC) or treated with crocin (HCC CR), sorafenib (HCC SB) separately or in combination (HCC CR SB). High magnification 40× and low magnification at 10×. Arrows point to representative areas of AHF).

Histopathological examination of liver tissue (FIG. 10) was performed to further investigate the therapeutic effects of crocin on DEN-induced HCC in rats. Liver sections were examined under light microscope to obtain representative images. In order to visualize cellular components and tissues under the microscope, sections were stained using Hematoxylin (H) which stains the nucleus with a blue color and with eosin (E) which stains the cytosol with a pink color. H&E are the standard stains used in histology. Control PBS group showed normal architecture and histology of animal liver, normal liver lobule with a central vein, hepatocytes are arranged in normal spans, radiating from the central vein. Histological examination also revealed that the intact core and normal vascular relationships between the portal tract and hepatic venules were evident. Histological evaluation of HCC groups demonstrated abnormal cell morphology which was consistent with the progression of HCC, where the liver cords appeared wider than normal liver plates, the normal architecture of the lobules were lost. Crocin either alone or in combination with sorafenib restored to a great degree the normal architecture of the liver in HCC groups.

Reticulin Staining

Figure 5:
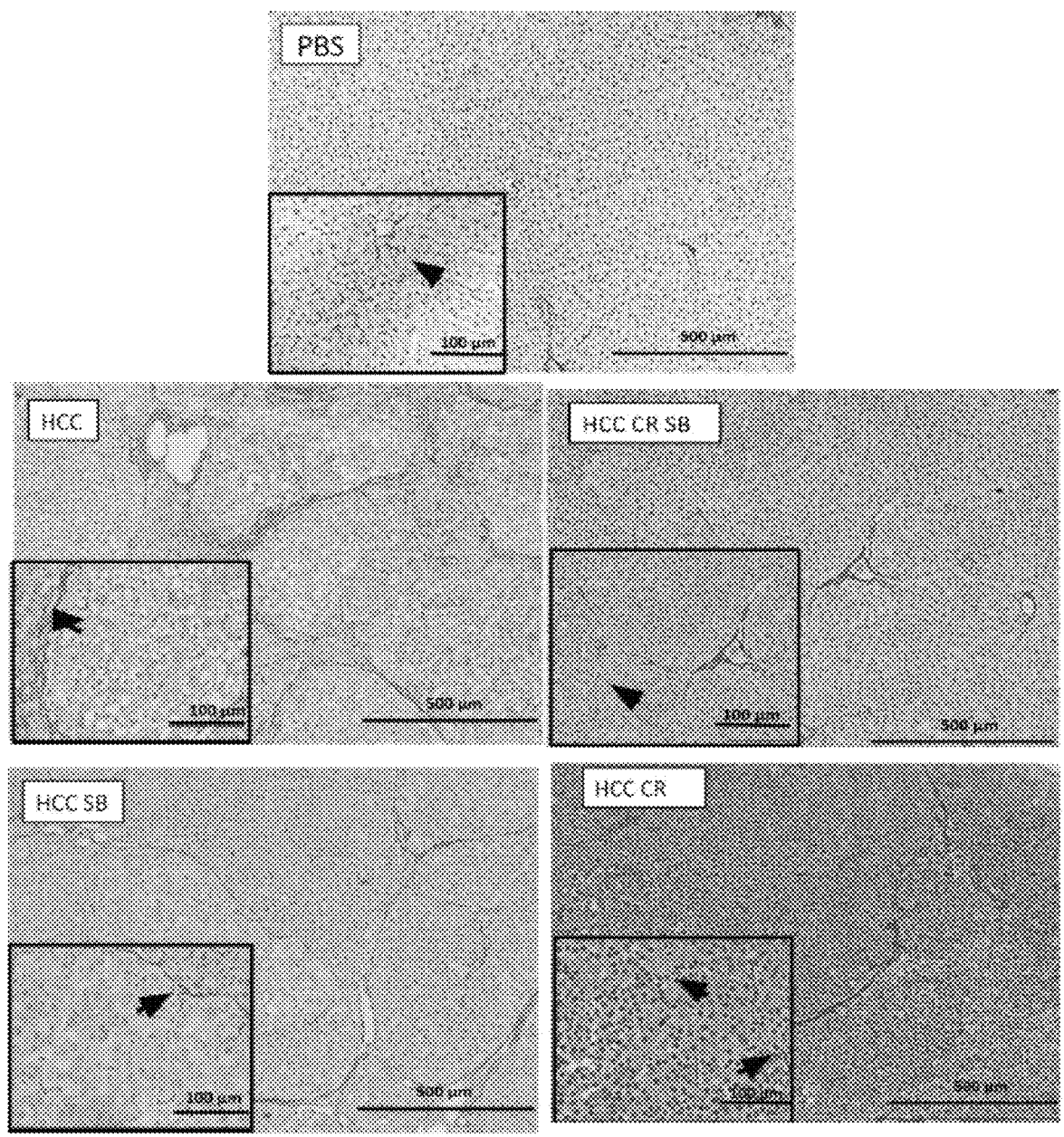
FIG. 5 includes reticulin staining livers from all groups. Sections from control groups (PBS), DEN-induced HCC in untreated rats (HCC) or treated with crocin (HCC CR), sorafenib (HCC SB) individually or in combination (HCC CR SB). High magnification 40× and low magnification at 10×. Arrows point to reticulin fibers.

Reticulin is an immunostain that is mostly used to investigate the liver histopathology. It helps visualizing the reticular fibers, which is a useful tool in diagnosing well differentiated HCC. Liver sections from all groups were processed and stained with reticulin and examined with light microscope (FIG. 5). Control PBS groups demonstrated a normal reticular network. Experimental HCC group showed apparent collapse of the reticulin network. Monotherapy with crocin alone (HCC+crocin) and in combination with sorafenib (HCC+crocin+sorafenib) recovered the damage done by the DEN-induction of cancer, fiber breakage appeared less often in comparison to HCC groups.

Figure 6:
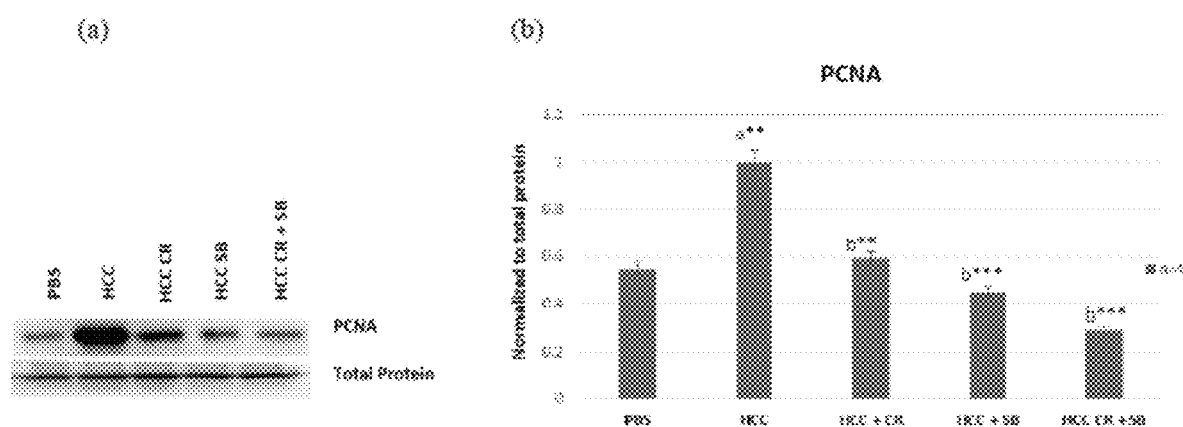
FIG. 6 illustrates how crocin inhibits proliferation of induced HCC. (a) Western blot where PCNA was assessed in control (PBS) and experimental groups DEN-induced HCC (HCC) or treated with crocin (HCC CR), sorafenib (HCC SB) separately or in combination (HCC CR SB). (b) Quantification plot where signals were quantified using ImageJ and normalized in accordance to the total protein from the liver. Results are expressed as mean±SD for n=4 animals from each group. Statistical significance was determined using Microsoft Excel Data Analysis Tool Pack t-test: two-sample assuming equal variance. a versus PBS, b versus HCC; *P<0.05, P<0.01, *P<0.001

Western blot analysis and quantification of PCNA highlights the significant ($P<0.01$) increase in PCNA expression in HCC animal livers in comparison to the control group, while treatment with crocin ($P<0.01$) either alone and in combination with sorafenib ($P<0.01$) significantly lowered the expression of PCNA. The combination of crocin and sorafenib yielded significant ($P<0.001$) lower levels of PCNA as compared to either crocin alone or sorafenib alone (FIG. 6).

Role of Crocin in Apoptosis

Figure 8:
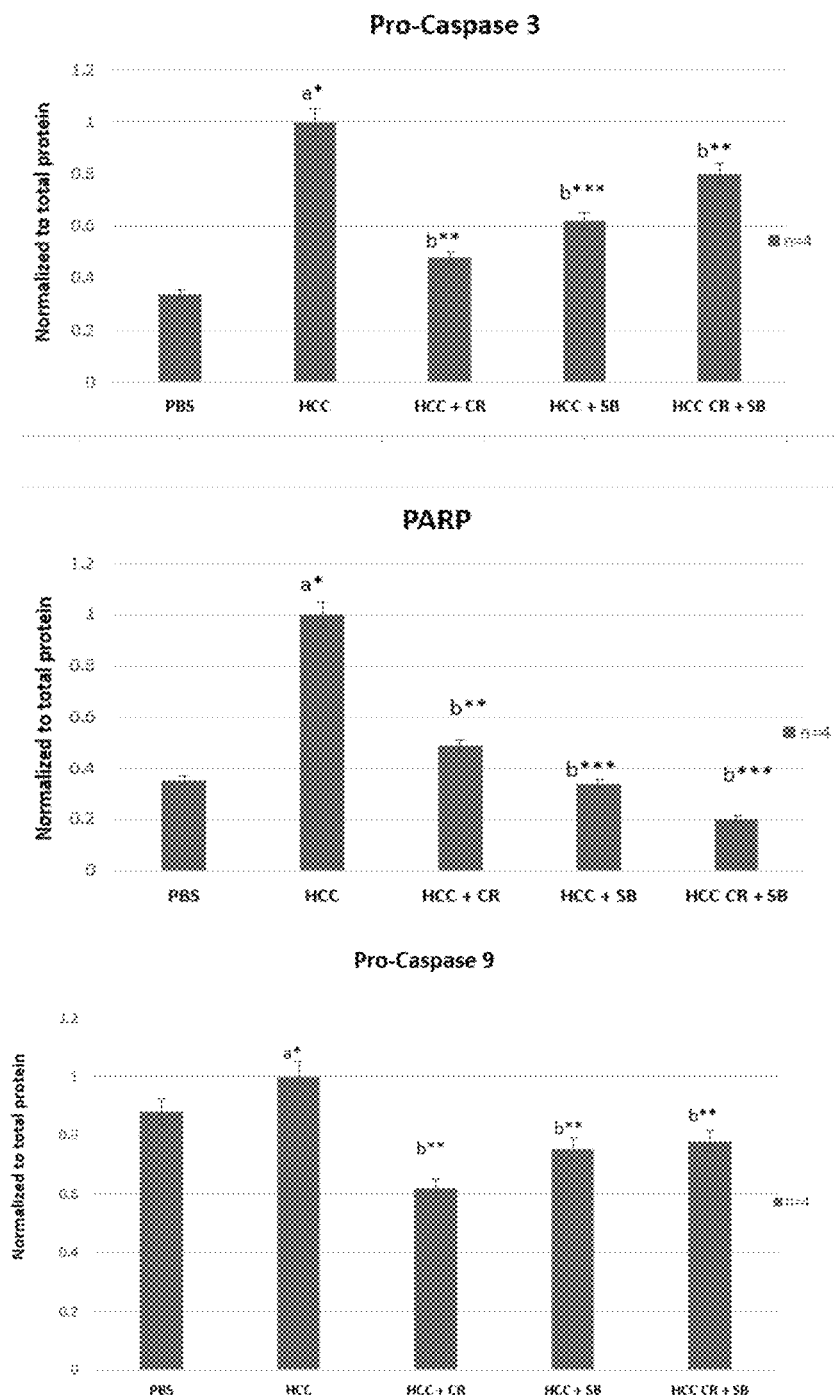
FIG. 8 is a quantification of Pro-Caspase-3, Pro-Caspase-3, PARP from control and experimental groups. Control group (PBS), DEN-induced HCC in untreated rats (HCC) or treated with crocin (HCC CR), sorafenib (HCC SB) separately or in combination (HCC CR SB). Band intensities were quantified using ImageJ and normalized in accordance to the total protein from the liver. Results are expressed as mean±SD for n=4 animals from each group. Statistical significance was determined using Microsoft Excel Data Analysis Tool Pack t-test: two-sample assuming equal variance. a versus PBS, b versus HCC; *P<0.05, P<0.01, *P<0.001
Figure 9:
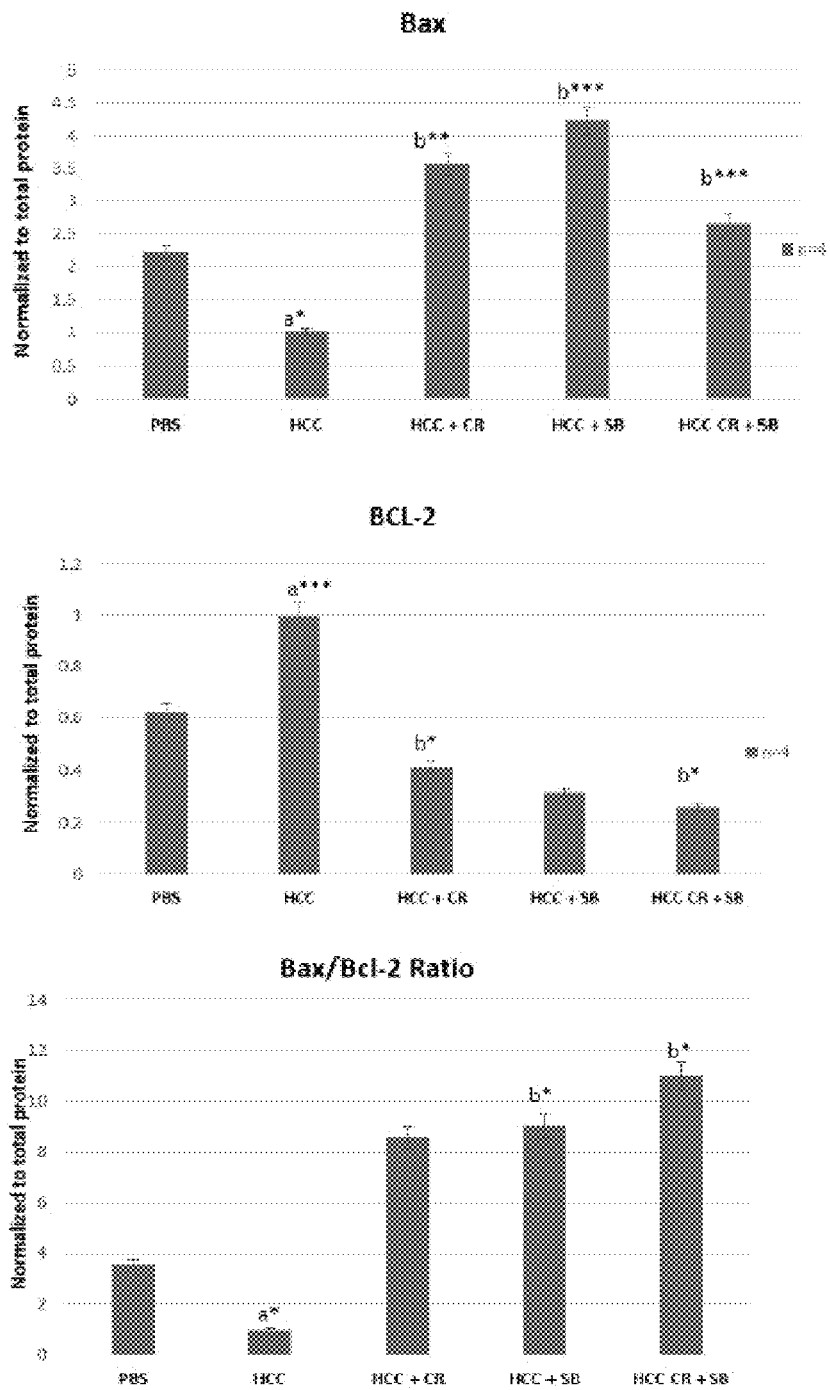
FIG. 9 is a quantification of Bax, Bcl-2, Bax/Bcl ratio from control and experimental groups. Sections from control groups (PBS), DEN-induced HCC in untreated rats (HCC) or treated with crocin (HCC CR), sorafenib (HCC SB) separately or in combination (HCC CR SB). Band intensities were quantified using ImageJ and normalized in accordance to the total protein from the liver. Results are expressed as mean±SD for n=4 animals from each group. Statistical significance was determined using Microsoft Excel Data Analysis Tool Pack t-test: two-sample assuming equal variance. a versus PBS, b versus HCC; *P<0.05, P<0.01, *P<0.001.

The role of crocin in the apoptotic pathway of DEN-induced HCC in animals was investigated by assessing the expression of key markers involved particularly in the mitochondria-mediated (intrinsic) apoptosis. The data collected here shows that treatment with crocin had a significant ($P<0.05$) effect on increasing the expression of the pro-apoptotic protein Bax which plays an important role in the activation of the pathway while the expression of the anti-apoptotic protein Bcl-2 was significantly ($P<0.05$) decreased compared to the HCC group. Data demonstrated that crocin given in combination with sorafenib had a stronger ($P<0.05$) effect on the DEN-induced HCC animals compared to either crocin alone or sorafenib alone. Multiple western blot experiments were completed to thoroughly investigate the role of crocin on apoptosis where results have confirmed that pro-caspase-3, pro-caspase-9, and PARP the activation of the intrinsic apoptotic pathway. The expression of these proteins was significantly (P<0.01, P<0.01, P<0.001, respectively) decreased in the crocin-treated group and when crocin was used in combination with sorafenib as compared to the HCC group alone proceeding treatment with crocin and with both crocin and sorafenib (FIG. 8, FIG. 9).

DISCUSSION

The liver is a complex organ that carries out essential functions that maintain homeostasis. Key biological processes that take place in the liver include the uptake, metabolism, and the excretion of various foreign materials. The liver is also involved in the immune response, phagocytosis and removal of microorganisms. It is also the site for metabolizing proteins, carbohydrates and fats. Routine analysis of liver function includes checking the levels of biomarkers including ALT and AST. These levels significantly reflect the level of liver damage and dysfunction. ALT is found in high concentrations in the liver; however, it is also found in other locations including the kidney and heart. In the cytoplasm of hepatocytes, ALT plays a key role as a catalyst in the transamination reaction. ALT is also involved in the transamination reaction and found in the mitochondria and cytoplasm of hepatocytes; however it is mainly concentrated in heart tissue. Slight damage to the liver will significantly elevate the levels of ALT and AST in the serum.

Figure 11:
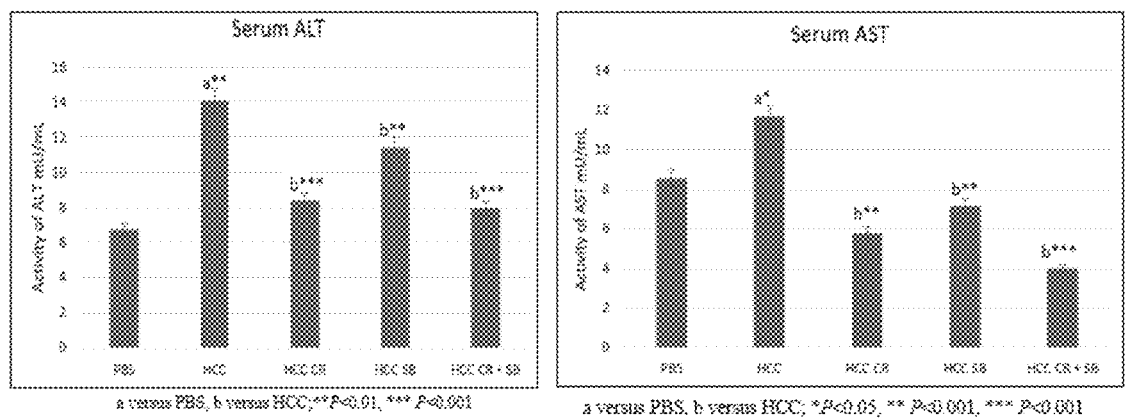
FIG. 11 illustrates the activity of liver enzymes (AST, ALT) measured in serum. (n=8). Statistical significance was determined using Microsoft Excel Data Analysis Too Pack, t-test; two-sample assuming equal variance (a versus PBS, b versus HCC, c versus HCC+SB; *P<0.05, **P<0.01, P<0.001).

Research investigating the chemo-preventative effect of saffron on DEN-induced HCC showed that saffron had significantly restored the levels of ALT and AST in rats. Treatment with sorafenib had a similar effect on the levels of these liver enzymes. ALT and AST were notably lower in the treated groups indicating amelioration of liver function. In the present study, the levels of liver serum enzymes both ALT and AST were higher in the DEN-induced HCC group in comparison to the PBS control group, which directly correlated with severe liver damage. Data collected in this investigation showcases that monotherapy with crocin had a great impact on lowering the levels of both ALT and AST in the blood in comparison to DEN-induced HCC rats (FIG. 11). Combination therapy with both crocin and sorafenib had a significantly stronger impact on decreasing the levels of these serum enzymes in comparison to sorafenib alone (P<0.05). Without being bound to any particular theory, this fact indicates that crocin and sorafenib work synergistically and with better efficacy to ameliorate the DEN-induced damage to the livers (FIG. 11).

Crocin's Impact of Ameliorating Histological Changes

The liver is divided into lobules, each one of these lobules has a hexagonal structure with a central vein and branches of hepatic artery, and bile duct. Hepatocytes are normally arranged in single-celled thick plates that are radiating from the central vein. To assess the effectiveness crocin, liver biopsies were analyzed. Liver biopsies are traditionally performed as a diagnostic tool to identify the cause and the severity of liver diseases. In this study, macroscopic nodules were observed in livers collected from DEN-treated animals as seen in (FIG. 3). Histopathological examination of livers in DEN-induced animals revealed clear features of HCC lesions showcasing trabecular pattern and characterized by clear cytoplasm. The normal hexagonal shape of hepatocytes is lost. Plates are no longer arranged in single-celled thick plates. Lymphocytic infiltration was observed. All of which indicate the development of HCC. Similar results were observed in other studies as well. Monotherapy with crocin alone and as an adjuvant with sorafenib has a significant impact on lowering the numbers of liver nodules observed (FIG. 4). Research using crocin coated D-MNPs nanoparticles to treat DEN-induced precancerous liver in mice showed that livers of animals treated with crocin showed apparent recovery of liver histology.

Crocin's Impact on The Reticular Network

The connective tissue is one of the four main types of tissues in the body. It has an important role in immune defense, growth and repair, and providing mechanical support. Connective tissue provides a backbone for epithelial tissue. It is composed mainly of the extracellular matrix and different types of cells. There are three different types of extracellular fibers including collagen, elastin and reticular fibers. Reticular fibers are mainly made up of type III collagen forming thin reticular network mainly found in the liver and muscle fibers. Reticulin staining has been shown to be a helpful tool in differential diagnosis to distinguish between well-differentiated HCC and benign liver lesions. In the case of HCC the reticular network is either completely lost or has an abnormal pattern. That pattern includes widen trabeculae with an increase in the thickness of cell layers.

Study conducted on rats aimed to uncover the changes in reticular fiber patterns in hepatic fibrosis induced by thioacetamide and bile duct ligation. A week after the induction of fibrosis the results showed a marked decrease in the reticular fiber suggesting the collapse of the reticular fiber network in response to liver damage reticular network. A paper reviewing the currently used inmmunohistochemistry stains for differential diagnosis of HCC revealed the reticulin stain of biopsy of HCC patients showed the loss of reticulin which confirms the stain's ability to be reliably used to diagnosis HCC and to differentiate the different phenotypes of liver cancers.

In this study, liver sections were processed and stained with reticulin and examined under light microscope (FIG. 5). PBS groups demonstrated an intact reticulin network with thin plates. Experimental HCC group showed abnormal patterns in the areas of HCC nodules, showing thicker plates with apparent collapse of the reticulin network. Monotherapy with crocin alone (HCC+crocin) and as an adjuvant with sorafenib (HCC+crocin+sorafenib) has significantly recovered the damage done by the DEN-induction of cancer; fiber breakage appeared less often in comparison to HCC groups. Results in the present study are consistent with the studies mentioned above.

Crocin's Anti-Cancer and Anti-Proliferative Impact on DEN-Induced HCC in Rats

Crocin Impact on Proliferation

PCNA has been found to play a vital role in many cellular processes including DNA replication, DNA repair, and cell cycle progression. Mutations during DNA replication will reflect in the post-translational modification of PCNA which in turn alters the function of PCNA. PCNA is a marker for proliferation, due to its role during replication. During replication PCNA molecules form a sliding clamp around the DNA helix, creating a platform to regulate the process of replication. Its expression is increased in breast and liver cancer metastasis. PCNA peaks during the S phase, therefore making it an indicator of cellular proliferation. Assessing the level of PCNA expression is used as a diagnostic and a prognostic tool to evaluate cancers. A study conducted on breast cancer patients revealed high expression of PCNA in cancer tissues of the patients in comparison to the adjacent normal tissues. Other investigation utilizing Sprague Dawley rats to evaluate the anti-tumor effects of bee honey showed high levels of PCNA expressed in the DEN-induced animals in comparison to the control groups. In the present study, western blot analysis demonstrated the levels of PCNA in DEN-induced HCC animals was significantly higher in comparison to the control groups. Treatment with crocin and with both crocin and sorafenib lead to the decrease in the expression of PCNA (FIG. 6). Crocin has been found to inhibit cell proliferation and induce apoptosis in A549 and SPC-A1 lung cancer cells. In another research on breast cancer cells, crocin inhibited proliferation by disrupting the microtubule network. Research investigating the anti-tumor effects of crocin on treating melanoma in C57BL/6 mice that were transplanted with B16G10 cancer cells showed that after a 21 days treatment period with crocin, the tumor was reduced and the survival time was significantly increased.

Western Blot Analysis

Crocin's Role in Inducing Apoptosis

Apoptosis, programmed cell death, is one of the most studied topic in cellular biology. It is an intricate process that happens both in physiological and pathological conditions. Apoptosis is essential to maintain homeostasis and regulate cellular development. Imbalances in apoptosis will contribute to the development of many disorders including autoimmune diseases and cancer. In the case of cancer, the equilibrium between cell-death and cell-division is lost. This problem arises because cancer cells are extremely smart and adaptive, have the ability to skip the death signal, and continue multiplying endlessly. This leads to the formation of clumps of mutated cells; tumors.

Two pathways are involved in activation of apoptosis: the extrinsic pathway which is switched on by different death receptors and the intrinsic pathway which is regulated by the mitochondria and leads to the release of apoptotic factors. Enzymes involved in both pathways play a key role in the activation and deactivation of apoptosis. The most important family of these enzymes are known as "caspases". They mainly function to cleave certain substrates leading to their activation. This study focused on investigating the intrinsic apoptotic pathway.

The intrinsic pathway is activated by either extra-cellular or intracellular stressors including; hypoxia, DNA damage, oxidative stress). These stimuli will cause changes in the permeability of the outer mitochondrial membrane which will cause the release of cytochrome c. This permeability is controlled by the BCL-2 proteins family, specifically Bcl-2 and Bax. Once released cytochrome c will activate Apaf-1 and pro-caspase-9 forming an apoptosome. Accumulation of pro-caspase-9 will activate the initiator caspase-9. Under normal circumstances the pro-apoptoic protein Bax binds with the anti-apoptotic protein Bcl-2 to control mitochondrial membrane permeability. Once cytochrome c is released it will activate executioner caspase -3 and the initiator caspase -9.

Under normal physiological conditions PARP functions to detect and repair DNA damage and plays an essential role in the regulation of apoptosis. Once activated, PARP will transfer NAD+ and binds PAR into DNA polymerase in order to repair problems that arise during DNA replication. Excessive activation of PARP will switch on the intrinsic apoptotic pathway. PARP is a pro-apoptotic signal, after PARP activation, PARP will move from the nucleus into the cytosol to interact with the outer mitochondrial membrane. This process will release apoptosis-inducing factors and the cell undergoes apoptosis.

Apoptosis is a key player in driving carcinogenesis and making cancer cells chemo-resistant to conventional therapeutic approaches. Cancer's ability to skip apoptosis is one of the prominent hallmarks of cancer. Research conducted on lung cancer cells tested the effect of saffron on inducing apoptosis on A549 cells and found that levels of caspases was upregulated in saffron treated cells. This suggests the activation of apoptosis in cancer cells which is attributed to treatment with saffron. In another study, DEN-induced HCC in Wistar rats that were treated with melatonin has been shown to activate apoptosis. This has been shown via the upregulation in the levels of caspases and the cleaved PARP, melatonin led to the increase in the Bax/Bcl-2 ratio. Research investigating the effect of glycerol treatment in Wistar rats showed the apoptosis was increased and it has been shown through the activation of caspase-3 and the increase of the Bax/Bcl-2 ratio as well. In a study investigating the effect of crocin, another main bioactive molecule in saffron, the compound was shown to induce apoptosis in HepG2 cells, where the ratio of Bax to Bcl-2 was increased, and caspase-3, caspase-9, were upregulated. Another investigation confirmed crocin's ability to activate apoptosis showed that using crocin as a preventive measure against lesions of liver cancer in Wistar rat significantly upregulated apoptosis in the livers of treated animals, as was demonstrated through histological examination with M30 Cyto-Death anti-body. Research efforts using crocin-coated D-MNPs showed that percent increase in cell death with crocin D-MNPs was highly significant when compared to DNE-injected mice. Crocin has also been shown to induce an autophagy-independent classical programmed cell death in colorectal cancer cells; HCT116 wild type and HCT116 p53-/-cell lines.

Figure 7:
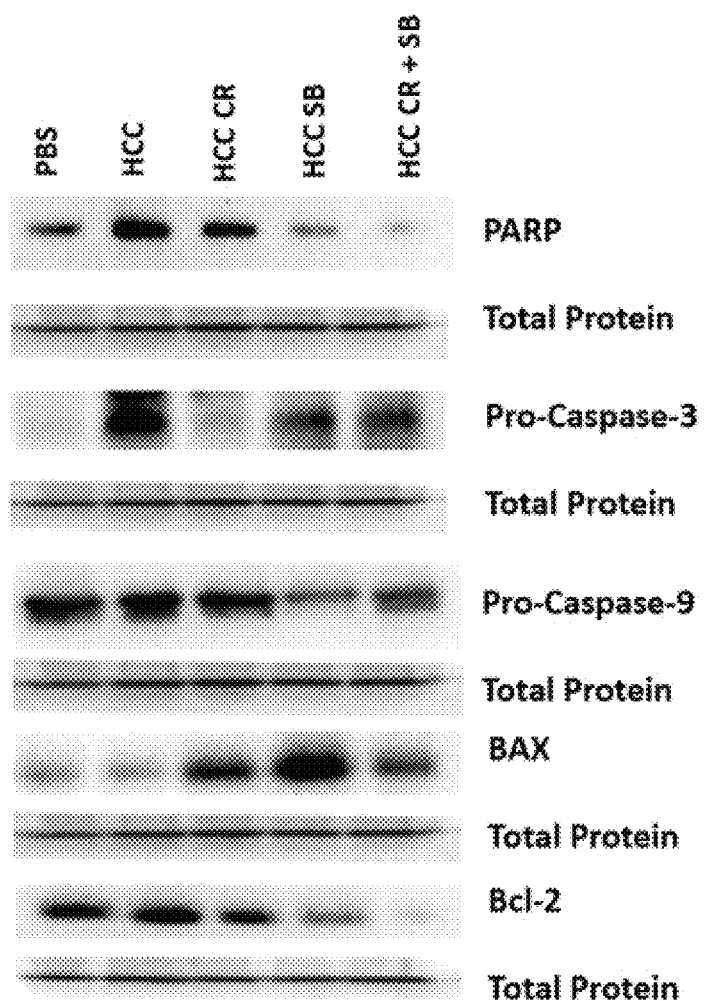
FIG. 7 is a western blot analysis of the key proteins involved in the intrinsic apoptotic pathway (PARP, Pro-Caspase-9, Pro-Caspase-3, Bax, Bcl-2) of livers from control and experimental groups. The analysis shows that crocin activates the intrinsic apoptotic pathway of DEN-induced HCC. Control group (PBS), DEN-induced HCC in untreated rats (HCC) or treated with crocin (HCC CR), sorafenib (HCC SB) individually or in combination (HCC CR SB).

In the present study, western blot analysis (FIGS. 7, 8, 9) demonstrated that treatment with crocin triggered the activation of the intrinsic apoptotic pathway. This has been concluded through measuring the expression of key players in the intrinsic pathway including Bax, Bcl-2, PARP, caspase-3 and caspase-9. Results in the current study showcased the upregulation of Bax and the downregulation of Bcl-2 as a result of the treatment with crocin in comparison with HCC rats. Therefore, the increase in the Bax/Bcl-2 ratio seemed to support this conclusion. Intriguingly, adjuvant treatment of crocin and sorafenib seemed to have a better effect in the activation of the intrinsic pathway over the treatment with crocin alone or sorafenib alone. Further investigation in the intrinsic pathway revealed the remarkable decrease in the expression of whole PARP, pro-caspase-3, and pro-caspase-9 in crocin treated rats in comparison with HCC animals. A study undertaken to evaluate saffron's anti-apoptotic effect on colorectal cancer cell lines demonstrated saffron induced p53-depedent caspase -3-activation in HCT116 cells.

DEFINITIONS

As used in this description and the accompanying claims, the following terms shall have the meanings indicated, unless the context otherwise requires:

As used herein, "treatment" is understood to refer to the administration of a drug or drugs to a patient suffering from cancer.

As used herein, the term "therapeutically effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

What is claimed is:

1. A method of treating, suppressing, or reducing the severity of a liver cancer in a subject, the method comprising:
   administering to the subject a first amount of sorafenib, and
   administering to the subject a second amount of a crocin or a pharmaceutically acceptable pro-drug thereof, wherein the crocin or a pharmaceutically acceptable pro-drug thereof and sorafenib are administered to the subject at a weight ratio of between 50:1 and 5:1,
   wherein the crocin or its pro-drug is administered first to sensitize the cancer cells prior to exposure to the sorafenib, and the sorafenib is administered second.

2. The method of claim 1, wherein the crocin is α-crocin.

3. The method of claim 1, where the crocin or its pro-drug and the sorafenib are compounded together in one composition including both compounds.

4. The method of claim 1, where the crocin or its pro-drug and the sorafenib are administered separately in separate pharmaceutical compositions.

5. The method of claim 1, where the crocin or its pro-drug and the sorafenib are administered in a sequential manner.

6. The method of claim 1, where the pro-drug is selected from the group consisting of a crocin salt, hydrate, hemiacetal, acetal, thioacetal, silylether, tautomer, isomer, and combinations thereof.

7. The method of claim 1, where the liver cancer is selected from the group consisting of hepatocellular carcinoma (HCC), fibrolamellar HCC, cholangiocarcinoma, angiosarcoma, a metastatic liver cancer, and combinations thereof.

8. The method of claim 1, where the liver cancer is hepatocellular carcinoma.

9. A therapeutic combination of drugs for the treatment of a liver cancer, the combination comprising:
   a crocin or a pharmaceutically acceptable pro-drug thereof, and
   sorafenib, wherein the crocin or a pharmaceutically acceptable pro-drug thereof and sorafenib are present at a weight ratio of between 50:1 and 5:1.

10. The therapeutic combination of drugs of claim 9, where the crocin is selected from the group consisting of monoglycosyl polyene esters of crocetin, diglycosyl polyene esters of crocetin, and combinations thereof.

11. The therapeutic combination of drugs of claim 9, where the crocin is α-crocin.

12. The therapeutic combination of drugs of claim 9, where the pro-drug is selected from the group consisting of a crocin salt, hydrate, hemiacetal, acetal, thioacetal, silylether, tautomer, isomer, and combinations thereof.

13. The therapeutic combination of drugs of claim 9, where the crocin and the sorafenib are compounded together in a same unitary pharmaceutical composition including both compounds.

14. The therapeutic combination of drugs of claim 9, where the crocin and the sorafenib are in separate pharmaceutical compositions.

15. A method of treating, suppressing, or reducing the severity of a liver cancer in a subject, the method comprising administering to a subject a therapeutically effective amount of the therapeutic combination of drugs of claim 9.

16. A method of treating, suppressing, or reducing the severity of a liver cancer in a subject, the method comprising:
   administering a first amount of sorafenib to the subject, and
   administering to the subject a second amount of a crocin, wherein the second amount of crocin and the first amount of sorafenib are within a weight ratio of 50:1 to 5:1 crocin to sorafenib,
   wherein the crocin is administered first to sensitize the cancer cells prior to exposure to the sorafenib, and the sorafenib is administered second.

17. The method of claim 16, wherein the crocin is α-crocin.

18. The method of claim 16, wherein the crocin and the sorafenib are compounded together in a same unitary pharmaceutical composition including both compounds.

* * * * *